US012594229B2

(12) United States Patent
Wu et al.

(10) Patent No.: US 12,594,229 B2
(45) Date of Patent: Apr. 7, 2026

(54) PERSONAL CARE COMPOSITIONS AND METHODS FOR THE SAME

(71) Applicant: Colgate-Palmolive Company, New York, NY (US)

(72) Inventors: Qiang Wu, Hillsborough, NJ (US); Thomas Boyd, Metuchen, NJ (US); Srdjan Maksimovic, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 727 days.

(21) Appl. No.: 17/250,411

(22) PCT Filed: Dec. 4, 2020

(86) PCT No.: PCT/US2020/070851
§ 371 (c)(1),
(2) Date: Jan. 19, 2021

(87) PCT Pub. No.: WO2021/127677
PCT Pub. Date: Jun. 24, 2021

(65) Prior Publication Data
US 2022/0401338 A1 Dec. 22, 2022

Related U.S. Application Data

(60) Provisional application No. 62/948,480, filed on Dec. 16, 2019.

(51) Int. Cl.
| | |
|---|---|
| *A61K 8/67* | (2006.01) |
| *A61K 8/92* | (2006.01) |
| *A61Q 19/08* | (2006.01) |

(52) U.S. Cl.
CPC .............. *A61K 8/673* (2013.01); *A61K 8/922* (2013.01); *A61Q 19/08* (2013.01)

(58) Field of Classification Search
CPC ........ A61K 8/675; A61K 8/673; A61K 8/922; A61K 2800/522; A61Q 19/00; A61Q 19/08
See application file for complete search history.

(56) References Cited

U.S. PATENT DOCUMENTS

| | | | |
|---|---|---|---|
| 5,916,573 | A | 6/1999 | Cleaves |
| 6,503,492 | B2 | 1/2003 | McGlone et al. |
| 6,673,756 | B2 | 1/2004 | Sonnenberg et al. |
| 8,147,883 | B1 | 4/2012 | Msika et al. |
| 8,623,335 | B2 | 1/2014 | Waddington |
| 8,920,853 | B2 | 12/2014 | Darsale |
| 9,629,856 | B2 | 4/2017 | Dreher |
| 9,867,774 | B1 | 1/2018 | Hakim |
| 10,172,786 | B2 | 1/2019 | Anastassov et al. |
| 10,238,745 | B2 | 3/2019 | Finley et al. |
| 10,456,345 | B2 | 10/2019 | Ross |
| 10,806,692 | B2 | 10/2020 | Guskey et al. |
| 10,806,769 | B2 | 10/2020 | Tian et al. |
| 12,097,280 | B2 | 9/2024 | Wu et al. |
| 2003/0235550 | A1 | 12/2003 | Pan et al. |
| 2004/0241254 | A1 | 12/2004 | Kopas et al. |
| 2005/0100524 | A1 | 5/2005 | Springstead |
| 2005/0266103 | A1 | 12/2005 | Yoder |
| 2006/0029657 | A1 | 2/2006 | Popp et al. |
| 2007/0224154 | A1 | 9/2007 | Brumbaugh et al. |
| 2008/0286390 | A1 | 11/2008 | Tanyi |
| 2010/0003292 | A1 | 1/2010 | Gautier et al. |
| 2011/0264059 | A1 | 10/2011 | Klofta et al. |
| 2012/0095087 | A1 | 4/2012 | Hyatt |
| 2013/0230609 | A1 | 9/2013 | Modak et al. |
| 2015/0182428 | A1 | 7/2015 | Schmit |
| 2016/0235661 | A1 | 8/2016 | Changoer et al. |
| 2016/0287658 | A1 | 10/2016 | Son et al. |
| 2016/0317419 | A1 | 11/2016 | Hakazaki et al. |
| 2016/0331675 | A1 | 11/2016 | Jamerson |
| 2017/0000717 | A1 | 1/2017 | Reynoso |
| 2017/0281718 | A1 | 10/2017 | Tian et al. |
| 2018/0049971 | A1 | 2/2018 | Druilhet |
| 2018/0263952 | A1 | 9/2018 | Bíróet al. |
| 2018/0284402 | A1 | 10/2018 | Hoag |
| 2019/0374552 | A1 | 12/2019 | Hoag |
| 2022/0023193 | A1 | 1/2022 | Wu et al. |
| 2022/0304915 | A1 | 9/2022 | Wu et al. |

(Continued)

FOREIGN PATENT DOCUMENTS

| | | |
|---|---|---|
| CN | 1679505 | 10/2005 |
| CN | 1883449 | 12/2006 |

(Continued)

OTHER PUBLICATIONS

International Search Report and the Written Opinion of the International Searching Authority issued in International Application PCT/US2020/070614 mailed Jan. 25, 2021.
Babaria, 2019, "48H Antiperspirant Deo", Mintel Database GNPD AN:6734525.
Cozietic, 2018, "Deodorant Spray", Mintel Database GNPD AN: 6211729.
Dr. Organic, 2015, "Deodorant Roll-On", Mintel Database GNPD AN:3560879.
National Medical Products Administration, 2021, "Technical Specification for Cosmetic Safety (Revised 2021 Edition)", pp. 1-8.
Esika, 2016, "Youth Activating Concentrated Facial Serum", Mintel Database GNPD AN: 4394087.
Esika, 2017, "Day Anti-Ageing Facial Global Treatment SPF 25", Mintel Database GNPD AN: 4778185.

(Continued)

*Primary Examiner* — Lezah Roberts

(57) ABSTRACT

Personal care compositions and methods for treating or reducing reactive oxygen species in or on skin are disclosed. The personal care composition may include a carrier, at least one plant oil, and at least one vitamin B compound. The at least one plant oil and the at least one vitamin B compound may be present in an effective amount to reduce reactive oxygen species in skin. The method may include contacting the personal care composition with the skin.

11 Claims, No Drawings

(56) References Cited

U.S. PATENT DOCUMENTS

| 2022/0304917 A1 | 9/2022 | Hernandez et al. |
| 2022/0401350 A1 | 12/2022 | Wu et al. |

FOREIGN PATENT DOCUMENTS

| CN | 101422200 | | 5/2009 | | |
| CN | 101843336 | * | 9/2010 | | |
| CN | 104371866 | | 2/2015 | | |
| CN | 106074280 | | 11/2016 | | |
| CN | 106420538 | | 2/2017 | | |
| CN | 106620079 | | 5/2017 | | |
| CN | 107365355 | | 11/2017 | | |
| CN | 108541775 | | 9/2018 | | |
| CN | 108619048 | | 10/2018 | | |
| CN | 108635267 | | 10/2018 | | |
| CN | 108703930 | | 10/2018 | | |
| CN | 108785192 | | 11/2018 | | |
| CN | 108785192 | A * | 11/2018 | ............ | A61K 8/922 |
| CN | 108977290 | * | 12/2018 | | |
| CN | 110115706 | | 8/2019 | | |
| EP | 0514576 | | 11/1992 | | |
| EP | 1561457 | | 8/2005 | | |
| EP | 2444081 | | 4/2012 | | |
| EP | 2404502 | | 9/2013 | | |
| EP | 3159012 | | 4/2017 | | |
| FR | 2956580 | | 8/2011 | | |
| FR | 2965477 | | 4/2012 | | |
| KR | 20030074510 | | 9/2003 | | |
| RO | 126918 | | 12/2011 | | |
| RU | 2459614 | | 8/2012 | | |
| RU | 2664694 | | 8/2018 | | |
| WO | 1999/027904 | | 6/1999 | | |
| WO | 2010/067206 | | 6/2010 | | |
| WO | 2013/149323 | | 10/2013 | | |
| WO | 2016/176485 | | 11/2016 | | |
| WO | 2016/197015 | | 12/2016 | | |
| WO | 2017/011785 | | 1/2017 | | |
| WO | 2017/173240 | | 10/2017 | | |
| WO | 2017/175126 | | 10/2017 | | |
| WO | 2017/178937 | | 10/2017 | | |
| WO | 2018/183151 | | 10/2018 | | |
| WO | 2019/136351 | | 7/2019 | | |
| WO | 2019/186544 | | 10/2019 | | |
| WO | 2019/234743 | | 12/2019 | | |
| WO | 2020/028991 | | 2/2020 | | |

OTHER PUBLICATIONS

High Beauty, 2019, "High Five Cannabis Facial Moisturizer", Mintel Database GNPD AN: 7038029.

International Search Report and the Written Opinion of the International Searching Authority issued in International Application PCT/US2020/070771 mailed Feb. 24, 2021.

International Search Report and the Written Opinion of the International Searching Authority issued in International Application PCT/US2020/070837 mailed Mar. 29, 2021.

International Search Report and the Written Opinion of the International Searching Authority issued in International Application PCT/US2020/070849 mailed Mar. 11, 2021.

International Search Report and the Written Opinion of the International Searching Authority issued in International Application PCT/US2020/070851 mailed Mar. 4, 2021.

Purity Cosmetics, 2016, "Repair Eye Cream", Mintel Database GNPD AN: 4274053.

Votary, 2019, "Super Boost Night Drops" Mintel Database GNPD AN: 6841777.

Qiu, Bingyi, Modern Cosmetic Science and Technology, vol. III, China Light Industry Press, Mar. 31, 2016, p. 727.

Oroian et al., "Antioxidants Characterization, Natural Sources, Extraction and Analysis", Food Research International, 74 (2015) 10-36.

Yang et al., "Synthesis of pyrrolidone carboxylic acid", Applied Chemical Industry, vol. 45, No. 4, Apr. 2016.

Shigabieva, 2014, "Colloidal-chemical properties of foaming and gel compositions with biologically active components: dissertation," Candidate of Chemical Sciences: Feb. 2011.—Kazan, 2014.—158 p., pp. 8, 10, 113, chapter 1.3.

International Search Report and the Written Opinion of the International Searching Authority issued in International Application PCT/US2018/062411 mailed Jun. 13, 2019.

Reinholtz et al., 2012, "Cathelicidin LL-37: An Antimicrobial Peptide with a Role in Inflammatory Skin Disease," Ann Dermatology 24(2):126-135.

Nindo et al., 2010, "Thermal Properties of Aloe Vera Powder and Rheology of Reconstituted Gels", Transactions of the ASABE, 53(4):1193-1200.

Raskin et al., 2004, "Can an apple a day keep the doctor away", Current Pharmaceutical Designs, 10:3419-3429.

Styrczewska et al., 2015, "Flax fiber hydrophobic extract inhibits human skin cells inflammation and causes remodeling of extracellular matrix and wound closure activation," BioMed Research International, 2015:1-15.

Tallarida, 2011, "Quantitative methods for assessing drug synergism, Genes & Cancer", 2(11):1003-1008.

Anonymous, "Aloe Vera," accessed on Mar. 20, 2024, Wikipedia, pp. 1-11 (Year: 2024).

Anonymous, "Flax," last edited Jan. 3, 2024; Wikipedia, https://en.wikipedia.org/wiki/Flax.

Anonymous, "Hemp," last edited Mar. 3, 2024; Wikipedia, https://en.wikipedia.org/wiki/Hemp.

Anonymous, "Scalp," accessed on Mar. 20, 2024, Wikipedia, pp. 1-5 (Year: 2024).

China National Institutes for Food and Drug Control, "The Announcement on Updating the Catalog of Raw Materials Banned for Cosmetics," National Medical Products Administration, (No. 74 of 2021), published May 28, 2021, pp. 1-6.

Shay & Company, 2023, https://shayandcompany.com/product/hemp-seed-butter-refined-non-gmo-halal/.

Singh et al. 2008, "Evaluation of anti-inflammatory activity of plant lipids containing a-linolenic acid," Indian Journal of Experimental Biology, 46:453-456.

Watzl et al. 1991, "Marijuana components stimulate human peripheral blood mononuclear cell secretion of interferon-gamma and suppress interleukin-1 alpha in vitro," International Journal of Immunopharmacology, 13(8):1091-1097.

Sigmaaldrich, 2022, HU-210, H-7909, https://www.sigmaaldrich.com/deepweb/assets/sigmaaldrich/product/documents/183/196/h7909dat.pdf.

Nallathambi, et al., "Anti-Inflammatory Activity in Colon Models Is Derived from Δ9-Tetrahydrocannabinolic Acid That Interacts with Additional Compounds in Cannabis Extracts" Cannabis and Cannabinoid Research. 2017 2:1, 167-182.

Peng, Guanjie et al., "Whitening Cosmetic Science and Technology," China Light Industry Press, 1st ed., Jun. 2019, pp. 197.

Yôko, Lino, "Bunny Girl's Carrot Beauty and Slimming Book," Guangxi Science and Technology Press, 1st ed., Sep. 2012, pp. 34.

Zhang, Weiming et al., "One Belt, One Road Economic Plants," Southeast University Press, 1st ed., Nov. 2017, pp. 222.

* cited by examiner

PERSONAL CARE COMPOSITIONS AND METHODS FOR THE SAME

BACKGROUND

Skin is often exposed to various environmental stressors, such as air pollution. One of the most harmful components of air pollution is particulate matter (PM). For example, exposure of skin to PM often results in skin damage through PM-induced oxidative stress. In PM-induced oxidative stress, PM deposited on skin reacts with the skin to generate reactive oxygen species (ROS) in and on the skin that may lead to oxidative cell damage and cell death.

What is needed, then, are personal care compositions incorporating improved benefit agents for treating ROS or preventing the generation of ROS in or on skin, and methods for the same.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a personal care composition including a carrier, at least one plant oil, and at least one vitamin B compound. The at least one plant oil and the at least one vitamin B compound may each be present in an effective amount to reduce reactive oxygen species in skin.

In at least one example, the at least one vitamin B compound may include one or more of the following: a vitamin B1 compound, a vitamin B2 compound, a vitamin B3 compound, a vitamin B5 compound, a vitamin B6 compound, or combinations thereof. For example, the at least on vitamin B compound includes a vitamin B3 compound. In another example, the at least one vitamin B compound consists of the vitamin B3 compound. In at least one example, the vitamin B3 compound includes, consists essentially of, or consists of niacinamide.

In at least one example, the at least one plant oil may include one or more of the following: palm kernel oil, coconut oil, avocado oil, canola oil, corn oil, cottonseed oil, olive oil, palm oil, high-oleic sunflower oil, mid-oleic sunflower oil, sunflower oil, palm stearin oil, palm kernel olein oil, safflower oil, babassu oil, sweet almond oil, castor oil, canola oil, soybean oil, olive oil, acai oil, andiroba oil, apricot kernel oil, argan oil, passion fruit oil, manila oil, mango oil, shea oil, macadamia nut oil, brazil nut oil, borage oil, copaiba oil, grape seed oil, buriti oil, sesame oil, flaxseed oil or linseed oil, blueberry oil, cranberry oil, blackberry oil, plum oil, raspberry oil, camelina oil, camellia oil, walnut oil, wheat germ oil, calendula oil, cherry kernel oil, cucumber seed oil, papaya oil, aloe vera oil, hemp oil, hemp seed oil, or combinations thereof.

In at least one example, the at least one plant oil includes flaxseed oil.

In at least one example, the at least one vitamin B compound and the at least one plant oil may be present in a ratio of from about 1:5 to about 1:20, optionally from about 1:9 to about 1:11, further optionally about 1:10.

In at least one example, a total weight of the at least one vitamin B compound and the at least one plant oil is less than or equal to about 0.5 weight %, optionally, less than or equal to about 0.1 weight %, less than or equal to about 0.01 weight %, less than or equal to about 0.001 weight %, or less than or equal to about 6.875E-5 weight %, based on a total weight of the personal care composition.

In at least one example, the at least one plant oil may include a manufactured oil. In at least another example, the at least one plant oil may include a natural oil.

In at least one example, the carrier is a solid carrier. In another example, the carrier is a liquid carrier.

The foregoing and/or other aspects and utilities embodied in the present disclosure may be achieved by providing a method for treating or reducing reactive oxygen species in or on skin. The method may include contacting the skin with any one or more of the personal care compositions disclosed herein.

The foregoing and/or other aspects and utilities embodied in the present disclosure may be achieved by providing any one of the personal care compositions disclosed herein for use in treating or reducing reactive oxygen species in or on skin.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that personal care compositions including a synergistic combination of flaxseed oil and hempseed oil significantly decreased the measured amount of reactive oxygen species (ROS) in or on skin, thereby demonstrating skin protecting and/or treating benefits against atmospheric or environmental pollution. The surprising and unexpected decrease in ROS was demonstrated when FSO and HSO were present in a ratio of about 1:1.

The present inventors have also surprisingly and unexpectedly discovered that personal care compositions including a synergistic combination of flaxseed oil and a vitamin B compound, such as niacinamide, significantly decreased the measured amount of ROS in or on skin, thereby demonstrating skin protecting and/or treating benefits against atmospheric or environmental pollution. The surprising and unexpected decrease in ROS was demonstrated when FSO and niacinamide were present in a ratio of about 10:1. The surprising and unexpected decrease in ROS was further demonstrated when FSO and niacinamide were present in a ratio of about 10:1, and delivered to cell models in a total amount of about 1.875E-5%, or about 1.25E-5, or less.

Compositions

Compositions disclosed herein may be or include a personal care product or a personal care composition thereof. For example, compositions disclosed herein may be a personal care composition, a personal care product, or form a portion of the personal care composition or the personal care product. As used herein, the term or expression "personal care composition" may refer to a composition for topical application to skin of mammals, especially humans. The personal care composition may generally be a leave-on personal care composition or rinse off personal care composition, and may include any product applied to a human body. The personal care composition is preferably a leave-on personal care composition. The personal care composition may be in any suitable form. Illustrative forms of the personal care composition may be or include, but is not limited to, a liquid, a lotion, a cream, a foam, a scrub, a gel, a soap bar, a toner, a substance or composition applied with an implement or via a face mask, or the like. Illustrative personal care compositions may be or include, but are not limited to, cleansers, leave-on skin lotions or creams, emulsion, shampoos, conditioners, shower gels, antiperspirants, deodorants, depilatories, lipsticks, foundations, mascara, sunless tanners, sunscreen lotions, body washes, soaps, including bar soaps and liquid soaps (e.g., liquid hand soaps), face washes, moisturizers, serums, spot treatments, cosmetics, or the like.

In an exemplary implementation, the compositions disclosed herein may be personal care compositions including a carrier, a vitamin B compound, and/or one or more plant oils. In one example, the personal care composition may include a carrier and a single plant oil. In another example, the personal care composition may include the carrier and at least two plant oils. In yet another example, the personal care composition may include the carrier and a vitamin B compound. In another example, the personal care composition may include the carrier, a vitamin B compound, and one or more plant oils. In a preferred implementation, the personal care composition includes the carrier and a synergistic amount and/or ratio of a vitamin B compound and one or more plant oils. For example, the preferred implementation may include the carrier and a synergistic amount and/or ratio of a vitamin B compound (e.g., niacinamide) and flaxseed oil.

The personal care compositions disclosed herein may be capable of or configured to significantly decrease the measured amount of reactive oxygen species (ROS) in skin. As such, the personal care composition disclosed herein may be capable of or configured to treat, decrease, reduce, or prevent damage to the skin and/or provide skin protecting benefits against atmospheric or environmental pollution by decreasing the measured amount of ROS in or on skin.

The personal care composition may include one or more vitamin B compounds. As used herein, the term or expression "one or more vitamin B compounds" or the like may refer to or include any one or more of the following: B1 compounds, B2 compounds, B3 compounds, such as niacinamide, nicotinyl alcohol, or nicotinic acid, or derivatives or salts thereof, B5 compounds, such as panthenol, pantothenic acid, pantothenyl, B6 compounds, such as pyroxidine, pyridoxal, pyridoxamine, carnitine, thiamine, riboflavin, or any combination thereof. In a preferred implementation, the vitamin B compound includes at least niacinamide. In at least one implementation, the vitamin B compound may consist of or consist essentially of niacinamide. For example, the personal care composition may include niacinamide and be free or substantially free of any one or more of the remaining vitamin B compounds or B3 compounds thereof.

In at least one implementation, any one or more of the vitamin B compounds may be present in the personal care composition in an effective amount or a therapeutically effective amount. As used herein, the expression or term "effective amount of one or more of the vitamin B compounds" or the like may refer to an amount of any one or more of the vitamin B compounds sufficient to interact or work synergistically with a plant oil to elicit a response (e.g., biological, medical, etc.) of a tissue, system, animal, or human that is being sought. For example, a vitamin B compound, such as niacinamide, may be present in the personal care composition in an effective amount to interact or work synergistically with a plant oil, such as flaxseed oil, to provide skin protection benefits against atmospheric or environmental pollution.

The amount or concentration of any one or more of the vitamin B compounds present in the personal care composition may vary widely. In at least one implementation, any one or more of the vitamin B compounds may be present in the personal care composition in an amount sufficient to deliver an effective amount and/or ratio, as disclosed herein, of the one or more vitamin B compounds to skin cells when applied to an outer surface of the skin or outer dermis. It should be appreciated that the amount or concentration of the one or more vitamin B compounds present in the personal care composition may be relatively greater than the effective amount, as penetration of the one or more vitamin B compounds from the outer dermis to the skin cells may be at least partially determined by varying factors, as is known by those having ordinary skill in the art.

In at least one implementation, the amount of any one or more of the vitamin B compounds (e.g., each or a combination) present in the personal care composition may be from greater than 0 weight % to less than or equal to 40 weight %, based on a total weight of the personal care composition. For example, any one or more of the vitamin B compounds may be present in the personal care composition in an amount of from greater than 0 weight %, about 1E-6 weight %, about 2E-6 weight %, about 3E-6 weight %, about 4E-6 weight %, about 5E-6 weight %, about 6E-6 weight %, about 6.25E-6 weight %, about 1E-5 weight %, about 2E-5 weight %, about 3E-5 weight %, about 4E-5 weight %, about 5E-5 weight %, about 6E-5 weight %, about 6.25E-5 weight %, about 1E-4, about 1.25E-4, about 0.01 weight %, about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, about 1 weight %, about 1.2 weight %, about 1.4 weight %, about 1.6 weight %, about 1.8 weight %, about 2 weight %, about 3 weight %, about 4 weight %, about 5 weight %, about 6 weight %, about 7 weight %, about 8 weight %, about 9 weight %, about 10 weight %, about 15 weight %, or about 20 weight % to about 25 weight %, about 30 weight %, about 35 weight %, about 40 weight %, based on a total weight of the personal care composition. In another example, any one or more of the vitamin B compounds may be present in the personal care composition in an amount of at least 1E-6 weight %, at least 2E-6 weight %, at least 3E-6 weight %, at least 4E-6 weight %, at least 5E-6 weight %, at least 6E-6 weight %, at least 6.25E-6 weight %, at least 1E-5 weight %, at least 2E-5 weight %, at least 3E-5 weight %, at least 4E-5 weight %, at least 5E-5 weight %, at least 6E-5 weight %, at least 6.25E-5 weight %, at least 1E-4, at least 1.25E-4, at least 0.001 weight %, at least 0.01 weight %, at least 0.1 weight %, at least 1.0 weight %, at least 1.5 weight %, at least 2.0 weight %, at least 2.5 weight %, at least 3.0 weight %, at least 3.5 weight %, at least 4.0 weight %, at least 5 weight %, at least 10 weight %, at least 20 at least %, at least 30 weight %, or more, based on a total weight of the personal care composition. In yet another example, any one or more of the vitamin B compounds may be present in the personal care composition in an amount of from greater than 0 weight % to less than 40 weight %, less than 35 weight %, less than 30 weight %, less than 25 weight %, less than 20 weight %, less than 15 weight %, less than 10 weight %, less than 9 weight %, less than 8 weight %, less than 7 weight %, less than 6 weight %, less than 5 weight %, less than 4 weight %, less than 3 weight %, less than 2 weight %, less than 1 weight %, less than 0.1 weight %, or less than 0.01 weight %, less than 0.001 weight %, less than 1.25E-4, less than 1E-4, less than 6.25E-5 weight %, less than 6E-5 weight %, less than 5E-5 weight %, less than 4E-5 weight %, less than 3E-5 weight %, less than 2E-5 weight %, less than 1E-5 weight %, less than 6.25E-6 weight %, less than 6E-6 weight %, less than 5E-6 weight %, less than 4E-6 weight %, less than 3E-6 weight %, less than 2E-6 weight %, or less than 1E-6 weight %, based on a total weight of the personal care composition. In yet another example, any one or more of the vitamin B compounds may be present in the personal care composition in an amount of from greater than 0 weight % to about 5 weight %, about 0.01 weight % to about 5 weight %, about 0.1 weight % to about 4.9 weight %, about 0.2 weight % to about 4.8 weight %, about 0.3 weight % to about 4.7 weight %, about 0.4 weight % to about 4.6 weight %, about 0.5 weight % to about 4.5 weight %, about 0.6 weight % to about 4.4 weight %, about 0.7 weight % to about 4.3 weight %, about 0.8 weight % to about 4.2 weight %, about 0.9 weight % to about 4.1 weight %, about 1 weight % to about 4 weight %, about 1.2 weight % to about 3.8 weight %, about 1.4 weight % to about 3.6 weight %, about 1.6 weight % to about 3.4 weight %, about 1.8 weight % to about 3.2 weight %, about 2 weight % to about 3 weight %, about 2.2 weight % to about 2.8 weight %, or about 2.4 weight % to about 2.6 weight %, based on a total weight of the personal care composition.

The personal care composition may include one or more plant oils. For example, the personal care composition may include a single plant oil or a combination of two or more plant oils. As used herein, "plant oil" may refer to a natural oil that is completely obtained from a plant, or a manufactured oil made by blending at least two components of oil (e.g., triglycerides, saturated and/or unsaturated fatty acids, etc.) to substantially mimic the composition of a natural plant oil or provide an oil substantially similar in composition to a plant oil. For example, a manufactured oil substantially similar in composition to a plant oil may include at least 50 weight %, at least 60 weight %, at least 70 weight %, at least 80 weight %, at least 90 weight %, at least 95 weight %, at least 98 weight %, at least 99 weight %, at least 99.5 weight %, at least 99.9 weight %, or 100 weight % of the components that are naturally found in the plant oil that the manufactured oil is designed to substantially mimic.

Illustrative plant oils may be or include, but are not limited to, palm kernel oil, coconut oil, avocado oil, canola oil, corn oil, cottonseed oil, olive oil, palm oil, high-oleic sunflower oil, mid-oleic sunflower oil, sunflower oil, palm stearin oil, palm kernel olein oil, safflower oil, babassu oil, sweet almond oil, castor oil, canola oil, soybean oil, olive oil, acai oil, andiroba oil, apricot kernel oil, argan oil, passion fruit oil, manila oil, mango oil, shea oil, macadamia nut oil, brazil nut oil, borage oil, copaiba oil, grape seed oil, buriti oil, sesame oil, flaxseed oil or linseed oil, blueberry oil, cranberry oil, blackberry oil, plum oil, raspberry oil, camelina oil, camellia oil, walnut oil, wheat germ oil, calendula oil, cherry kernel oil, cucumber seed oil, papaya oil, aloe vera oil, hemp oil, hemp seed oil, or the like, or mixtures or combinations thereof. In at least one implementation, the personal care composition includes a synergistic combination of at least two plant oils. For example, the personal care composition includes a synergistic combination of flaxseed oil (FSO) and hempseed oil (HSO). In a preferred implementation, the personal care composition includes a synergistic combination of at least one plant oil and a vitamin B compound, such as niacinamide. For example, the personal care composition includes a synergistic combination of flaxseed oil and niacinamide.

In at least one implementation, any one or more of the plant oils may be present in the personal care composition in an effective amount or a therapeutically effective amount. As used herein, the expression or term "effective amount of one or more plant oils" or the like may refer to an amount of one or a first plant oil sufficient to interact or work synergistically with another or second plant oil and/or a vitamin B compound to elicit a response (e.g., biological, medical, etc.) of a tissue, system, animal, or human that is being sought.

For example, a first plant oil, such as FSO, may be present in the personal care composition in an effective amount to interact or work synergistically with a second plant oil, such as HSO, to provide skin protection benefits against atmospheric or environmental pollution. In another example, a first plant oil, such as FSO, may be present in the personal care composition in an effective amount to interact or work synergistically with a vitamin B compound, such as niacinamide, to provide skin protection benefits against atmospheric or environmental pollution.

The amount or concentration of any one or more of the plant oils present in the personal care composition may vary widely. In at least one implementation, any one or more of the plant oils may be present in the personal care composition in an amount sufficient to deliver an effective amount and/or ratio, as disclosed herein, of the one or more plant oils to skin cells when applied to an outer surface of the skin or outer dermis. It should be appreciated that the amount or concentration of the one or more plant oils present in the in the personal care composition may be relatively greater than the effective amount, as penetration of the one or more plant oils from the outer dermis to the skin cells may be at least partially determined by varying factors, as is known by those having ordinary skill in the art.

In at least one implementation, the amount of any one or more of the plant oils (e.g., each or a combination) present in the personal care composition may be from greater than 0 weight % to less than or equal to 40 weight %, based on a total weight of the personal care composition. For example, any one or more of the plant oils may be present in the personal care composition in an amount of from greater than 0 weight %, about 1E-5 weight %, about 2E-5 weight %, about 3E-5 weight %, about 4E-5 weight %, about 5E-5 weight %, about 6E-5 weight %, about 6.25E-5 weight %, about 1E-4, about 1.25E-4, about 0.01 weight %, about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, about 1 weight %, about 1.2 weight %, about 1.4 weight %, about 1.6 weight %, about 1.8 weight %, about 2 weight %, about 3 weight %, about 4 weight %, about 5 weight %, about 6 weight %, about 7 weight %, about 8 weight %, about 9 weight %, about 10 weight %, about 15 weight %, or about 20 weight % to about 25 weight %, about 30 weight %, about 35 weight %, about 40 weight %, based on a total weight of the personal care composition. In another example, any one or more of the plant oils may be present in the personal care composition in an amount of at least 1E-5 weight %, at least 2E-5 weight %, at least 3E-5 weight %, at least 4E-5 weight %, at least 5E-5 weight %, at least 6E-5 weight %, at least 6.25E-5 weight %, at least 1E-4, at least 1.25E-4, at least 0.001 weight %, at least 0.01 weight %, at least 0.1 weight %, at least 1.0 weight %, at least 1.5 weight %, at least 2.0 weight %, at least 2.5 weight %, at least 3.0 weight %, at least 3.5 weight %, at least 4.0 weight %, at least 5 weight %, at least 10 weight %, at least 20 at least %, at least 30 weight %, or more, based on a total weight of the personal care composition. In yet another example, any one or more of the plant oils may be present in the personal care composition in an amount of from greater than 0 weight % to less than 40 weight %, less than 35 weight %, less than 30 weight %, less than 25 weight %, less than 20 weight %, less than 15 weight %, less than 10 weight %, less than 9 weight %, less than 8 weight %, less than 7 weight %, less than 6 weight %, less than 5 weight %, less than 4 weight %, less than 3 weight %, less than 2 weight %, less than 1 weight %, less than 0.1 weight %, or less than 0.01 weight %, less than 0.001 weight %, less than 1.25E-4, less than 1E-4, less than 6.25E-5 weight %, less than 6E-5 weight %, less than 5E-5 weight %, less than 4E-5 weight %, less than 3E-5 weight %, less than 2E-5 weight %, or less than 1E-5 weight %, based on a total weight of the personal care composition. In yet another example, any one or more of the plant oils may be present in the personal care composition in an amount of from greater than 0 weight % to about 5 weight %, about 0.01 weight % to about 5 weight %, about 0.1 weight % to about 4.9 weight %, about 0.2 weight % to about 4.8 weight %, about 0.3 weight % to about 4.7 weight %, about 0.4 weight % to about 4.6 weight %, about 0.5 weight % to about 4.5 weight %, about 0.6 weight % to about 4.4 weight %, about 0.7 weight % to about 4.3 weight %, about 0.8 weight % to about 4.2 weight %, about 0.9 weight % to about 4.1 weight %, about 1 weight % to about 4 weight %, about 1.2 weight % to about 3.8 weight %, about 1.4 weight % to about 3.6 weight %, about 1.6 weight % to about 3.4 weight %, about 1.8 weight % to about 3.2 weight %, about 2 weight % to about 3 weight %, about 2.2 weight % to about 2.8 weight %, or about 2.4 weight % to about 2.6 weight %, based on a total weight of the personal care composition.

As discussed above, the personal care composition may include a synergistic combination of at least two plant oils. For example, the personal care composition may include a synergistic combination of a first plant oil and a second plant oil. In at least one implementation, a first plant oil and a second plant oil may be present in an effective ratio (i.e., concentration, weight, or volume ratio) or a therapeutically effective ratio (i.e., concentration, weight, or volume ratio) to elicit a response (e.g., biological medical, etc.) of a tissue, system, animal, or human that is being sought. For example, the first plant oil, such as FSO, and the second plant oil, such as HSO, may be present in an effective concentration, weight, or volume ratio or a therapeutically effective concentration, weight, or volume ratio to provide skin protection and/or healing benefits against atmospheric or environmental pollution.

The personal care composition may also include a synergistic combination of one or more vitamin B compounds and at least one plant oil. For example, the personal care composition may include a synergistic combination of a vitamin B compound, such as niacinamide, and a plant oil. In at least one implementation, the vitamin B compound and the plant oil may be present in an effective ratio (i.e., concentration, weight, or volume ratio) or a therapeutically effective ratio (i.e., concentration, weight, or volume ratio) to elicit a response (e.g., biological medical, etc.) of a tissue, system, animal, or human that is being sought. For example, the vitamin B compound, such as niacinamide, and the plant oil, such as FSO, may be present in an effective concentration, weight, or volume ratio or a therapeutically effective concentration, weight, or volume ratio to provide skin protection and/or healing benefits against atmospheric or environmental pollution.

In at least one implementation, the concentration, weight, or volume ratio of a first plant oil to a second plant oil may be from about 0.1:1 to about 5:1. For example, the concentration, weight, or volume ratio of the first plant oil to the second plant oil may be from about 0.1:1, about 0.2:1, about 0.3:1, about 0.4:1, about 0.5:1, about 0.6:1, about 0.7:1, about 0.8:1, about 0.9:1, or about 1.0:1 to about 1.1:1, about 1.2:1, about 1.3:1, about 1.4:1, about 1.5:1, about 1.6:1, about 1.7:1, about 1.8:1, about 1.9:1, about 2.0:1, about 2.1:1, about 2.2:1 to about 2.3:1, about 2.4:1, about 2.5:1, about 2.6:1, about 2.7:1, about 2.8:1, about 2.9:1, about 3.0:1, about 3.1:1, about 3.2:1, about 3.3:1, about 3.4:1, about 3.5:1, about 3.6:1, about 3.7:1, about 3.8:1, about 3.9:1, about 4:1, about 4.1:1, about 4.2:1, about 4.3:1, about 4.4:1, about 4.5:1, about 4.6:1, about 4.7:1, about 4.8:1, about 4.9:1, or about 5:1. In another example, the concentration, weight, or volume ratio of the first plant oil to the second plant oil, or the plant oil to niacinamide, may be from greater than or equal to about 0.1:1 to less than or equal to about 0.2:1, less than or equal to about 0.3:1, less than or equal to about 0.4:1, less than or equal to about 0.5:1, less than or equal to about 0.6:1, less than or equal to about 0.7:1, less than or equal to about 0.8:1, less than or equal to about 0.9:1, less than or equal to about 1.0:1, less than or equal to about 1.1:1, less than or equal to about 1.2:1, less than or equal to about 1.3:1, less than or equal to about 1.4:1, less than or equal to about 1.5:1, less than or equal to about 1.6:1, less than or equal to about 1.7:1, less than or equal to about 1.8:1, less than or equal to about 1.9:1, less than or equal to about 2.0:1, less than or equal to about 2.1:1, less than or equal to about 2.2:1 to less than or equal to about 2.3:1, less than or equal to about 2.4:1, less than or equal to about 2.5:1, less than or equal to about 2.6:1, less than or equal to about 2.7:1, less than or equal to about 2.8:1, less than or equal to about 2.9:1, less than or equal to about 3.0:1, less than or equal to about 3.1:1, less than or equal to about 3.2:1, less than or equal to about 3.3:1, less than or equal to about 3.4:1, less than or equal to about 3.5:1, less than or equal to about 3.6:1, less than or equal to about 3.7:1, less than or equal to about 3.8:1, less than or equal to about 3.9:1, less than or equal to about 4:1, less than or equal to about 4.1:1, less than or equal to about 4.2:1, less than or equal to about 4.3:1, less than or equal to about 4.4:1, less than or equal to about 4.5:1, less than or equal to about 4.6:1, less than or equal to about 4.7:1, less than or equal to about 4.8:1, less than or equal to about 4.9:1, or less than or equal to about 5:1. In yet another example, the concentration, weight, or volume ratio of the first plant oil to the second plant oil may be from greater than or equal to about 0.1:1, greater than or equal to about 0.2:1, greater than or equal to about 0.3:1, greater than or equal to about 0.4:1, greater than or equal to about 0.5:1, greater than or equal to about 0.6:1, greater than or equal to about 0.7:1, greater than or equal to about 0.8:1, greater than or equal to about 0.9:1, greater than or equal to about 1.0:1, greater than or equal to about 1.1:1, greater than or equal to about 1.2:1, greater than or equal to about 1.3:1, greater than or equal to about 1.4:1, greater than or equal to about 1.5:1, greater than or equal to about 1.6:1, greater than or equal to about 1.7:1, greater than or equal to about 1.8:1, greater than or equal to about 1.9:1, greater than or equal to about 2.0:1, greater than or equal to about 2.1:1, greater than or equal to about 2.2:1 to greater than or equal to about 2.3:1, greater than or equal to about 2.4:1, greater than or equal to about 2.5:1, greater than or equal to about 2.6:1, greater than or equal to about 2.7:1, greater than or equal to about 2.8:1, greater than or equal to about 2.9:1, greater than or equal to about 3.0:1, greater than or equal to about 3.1:1, greater than or equal to about 3.2:1, greater than or equal to about 3.3:1, greater than or equal to about 3.4:1, greater than or equal to about 3.5:1, greater than or equal to about 3.6:1, greater than or equal to about 3.7:1, greater than or equal to about 3.8:1, greater than or equal to about 3.9:1, greater than or equal to about 4:1, greater than or equal to about 4.1:1, greater than or equal to about 4.2:1, greater than or equal to about 4.3:1, greater than or equal to about 4.4:1, greater than or equal to about 4.5:1, greater than or equal to about 4.6:1, greater than or equal to about 4.7:1, greater than or equal to about 4.8:1, or greater than or equal to about 4.9:1 to less than or equal to about 5:1.

In a particular implementation, the concentration, weight, or volume ratio of the first plant oil to the second plant oil may be from about 0.5:1 to about 4:1, more preferably from about 1:1 to about 2:1. For example, the concentration, weight, or volume ratio of flaxseed oil to hemp seed oil may be from about 0.5:1 to about 4:1, more preferably from about 1:1 to about 2:1.

In at least one implementation, the concentration, weight, or volume ratio of the plant oil to the vitamin B compound may be from about 5:1 to about 20:1. For example, the concentration, weight, or volume ratio of the plant oil to the vitamin B compound may be from about 5:1, about 5.5:1, about 6:1, about 6.5:1, about 7:1, about 7.5:1, about 8:1, about 8.5:1, about 9:1, about 9.5:1, about 9.6:1, about 9.7:1, about 9.8:1, or about 9.9:1 to about 10:1, about 10.1:1, about 10.2:1, about 10.3:1, about 10.4:1, about 10.5:1, about 11:1, about 12:1, about 13:1, about 14:1, about 15:1, about 16:1, about 17:1, about 18:1, about 19:1, or about 20:1. In another example, the concentration, weight, or volume ratio of the plant oil to the vitamin B compound may be from greater than about 5:1 to less than or equal to about 20:1, less than or equal to about 15:1, less than or equal to about 12:1, less than or equal to about 11:1, less than or equal to about 10.5:1, less than or equal to about 10:1, less than or equal to about 9.5:1, less than or equal to about 9:1, less than or equal to about 8:1, less than or equal to about 7:1, or less than or equal to about 6:1. In yet another example, the concentration, weight, or volume ratio of the plant oil to the vitamin B compound may be from greater than or equal to about 5:1, greater than or equal to about 6:1, greater than or equal to about 7:1, greater than or equal to about 8:1, greater than or equal to about 9:1, greater than or equal to about 9.5:1, greater than or equal to about 10:1 to less than or equal to about 20:1. In a particular implementation, the concentration, weight, or volume ratio of the plant oil to the vitamin B compound may be from about 9:1 to about 11:1, more preferably about 9.5:1 to about 10.5:1, even more preferably about 10:1. For example, the concentration, weight, or volume ratio of flaxseed oil to the vitamin B compound, such as niacinamide, may be from about 9:1 to about 11:1, more preferably about 9.5:1 to about 10.5:1, even more preferably about 10:1.

The total amount of active ingredients in the personal care composition may vary widely. It should be appreciated that the active ingredients of the personal care compositions disclosed herein may include those ingredients capable of or configured to provide skin protection against environmental pollution and/or against the generation of reactive oxygen species in skin. In at least one example, the active ingredients include, consist essentially of, or consist of the plant oils and/or the vitamin B compounds. For example, the active ingredients of the personal care composition may be any combination of one or more plant oils and/or one or more vitamin B compounds. In a preferred implementation, the active ingredients include a plant oil and a vitamin B compound. For example, the active ingredients include flaxseed oil and niacinamide. In at least one implementation, the total amount of the active ingredients present in the personal care composition may be from greater than 0 weight % to less than or equal to about 40 weight %, less than or equal to about 30 weight %, less than or equal to about 20 weight %, less than or equal to about 10 weight %, less than or equal to about 9 weight %, less than or equal to about 8 weight %, less than or equal to about 7 weight %, less than or equal to about 6 weight %, less than or equal to about 5 weight %, less than or equal to about 4 weight %, less than or equal to about 3 weight %, less than or equal to about 2 weight %, less than or equal to about 1 weight %, less than or equal to about 0.9 weight %, less than or equal to about 0.8 weight %, less than or equal to about 0.7 weight %, less than or equal to about 0.6 weight %, less than or equal to about 0.5 weight %, less than or equal to about 0.4 weight %, less than or equal to about 0.3 weight %, less than or equal to about 0.2 weight %, less than or equal to about 0.1 weight %, less than or equal to about 0.01 weight %, less than or equal to about 0.001 weight %, less than or equal to about 0.0001 weight %, less than or equal to about 9E-5 weight %, less than or equal to about 8E-5 weight %, less than or equal to about 7E-5 weight %, less than or equal to about 6.875E-5 weight %, less than or equal to about 6.5E-5 weight %, less than or equal to about 6E-5 weight %, less than or equal to about 5.5E-5 weight %, less than or equal to about 5E-5 weight %, or less than or equal to about 4.5E-5 weight %, based on a total weight of the personal care composition. In an exemplary implementation, the active ingredients include flaxseed oil and niacinamide in a total weight % of about 6.875E-5-5%, based on a total weight of the personal care composition.

The personal care composition may include the one or more plant oils and/or the one or more vitamin B compounds, mixed with, dissolved in, combined with, or otherwise contacted with the carrier or one or more excipients. In at least one implementation, the carrier may be capable of or configured to store, entrain, or otherwise contain the one or more plant oils and/or the one or more vitamin B compounds, and deliver the one or more plant oils and/or the one or more vitamin B compounds to one or more tissues, such as skin. It should be appreciated that the components or contents of the carrier and the respective amount of each of the components of the carrier may be at least partially determined by the type or use of the personal care product or the composition thereof. Illustrative personal care products or compositions thereof may include, but are not limited to, cleansers, leave-on skin lotions or creams, emulsion, shampoos, conditioners, shower gels, antiperspirants, deodorants, depilatories, lipsticks, foundations, mascara, sunless tanners, sunscreen lotions, body washes, soaps, including bar soaps and liquid soaps (e.g., liquid hand soaps), face washes, moisturizers, serums, spot treatments, cosmetics, or the like. In a preferred implementation, the personal care product or the composition thereof that includes the one or more plant oils and/or the one or more vitamin B compounds are solid cleansing compositions, such as bar soaps.

In at least one implementation, the personal care product or the composition thereof may be a skin care product. Illustrative skin care product may be or include, but are not limited to, a lotion, a cosmetic, a sunscreen, or the like. The carrier of the skin care product may include, but is not limited to, any one or more of surfactants, conditioning agents, moisturizers, sunscreens, UV absorbers, antioxidants, enzymes and/or other proteins, vitamins, antibacterial agents, odor reducing agents, steroids, anti-inflammatory agents, naturally and/or non-naturally occurring humectants, skin lipid fluidizers, occlusive agents, amino acids, physical and/or chemical exfoliants, skin whiteners, anti-aging, antiperspirant actives, or the like, or any combination thereof.

In at least one implementation, the personal care product or the composition thereof may be a personal hand and/or body cleansing composition or a personal hand and/or body conditioning composition. Illustrative personal hand and/or body cleansing or conditioning compositions may include, but are not limited to, liquid soaps, bar soaps, body washes, shower gels, lotions, and the like. In a preferred implementation, the personal hand and/or body cleansing or conditioning composition is a solid personal hand and/or solid body cleansing or conditioning composition, such as bar soap. The carrier for the personal hand and/or body cleansing composition or the personal hand and/or body conditioning composition may include, but is not limited to, any one or more of fragrances, essential oils, emulsifying agents, thickening agents, colorants, surfactants, natural actives, therapeutic actives, stain prevention actives, antimicrobial agents, vitamins, natural extracts, amino acids, enzymes and/or other proteins, abrasives, odor control agents, conditioning agents, moisturizers, humectants, occlusive agents, skin lipid fluidizers, lipophilic actives, hydrophilic materials, pearlizers, opacifying agents, sodium soaps, titanium dioxide, fragrances, or the like, or any mixture or combination thereof, in addition to any one or more of the other carrier components as discussed above.

The carrier may be hydrophilic or hydrophobic. The carrier may be anhydrous. The carrier may be a liquid or a solid at room temperature. The carrier may have a viscosity of from about 2,000 centipoise (cP) to about 100,000 cP. For example, the carrier for a shower gel may have a viscosity of from about 2,000 cP to about 16,000 cP. In another example, the carrier for a lotion may have a viscosity of from about 10,000 cP to about 100,000 cP. Accordingly, it should be appreciated that the viscosity of the carrier may vary and may at least partially depend on the type of personal care composition. In an exemplary implementation, the carrier is a solid at room temperature.

Unless otherwise specifically identified, the ingredients for use in the compositions and formulations of the compositions disclosed herein are preferably cosmetically acceptable ingredients. As used herein, the expression "cosmetically acceptable" may refer to a component or ingredient that is suitable for use in a formulation for topical application to human skin. A cosmetically acceptable excipient, may refer to an excipient that is suitable for external application in the amounts and concentrations contemplated in the formulations of the compositions disclosed herein, and includes for example, excipients which are "Generally Recognized as Safe" (GRAS) by the United States Food and Drug Administration (FDA).

Methods

The present disclosure may provide methods for preparing a personal care product or a personal care composition thereof. The method may include mixing, stirring, combining, or otherwise contacting a carrier, one or more plant oils, and/or one or more vitamin B compounds with one another. In at least one example, the carrier may be a solid cleansing composition, such as a bar soap.

The present disclosure may provide methods for treating, decreasing, reducing, or preventing damage to the skin and/or providing skin protection benefits against atmospheric or environmental pollution by reducing reactive oxygen species in and on the skin. The method may include contacting an effective amount of any one or more of the personal care compositions disclosed herein with the skin. For example, the method may include contacting an effective amount of a personal care composition including a synergistic amount of one or more plant oils and/or one or more vitamin B compounds with the skin. The one or more plant oils may include flaxseed oil or a combination of flaxseed oil and hempseed oil. The one or more vitamin B compounds may include niacinamide. In at least one example, the plant oil includes flaxseed oil, and the vitamin B compound includes niacinamide.

The present disclosure may also provide a personal care composition including a carrier, one or more plant oils, and/or one or more vitamin B compounds for use in treating, decreasing, reducing, or preventing damage to the skin and/or providing skin protection benefits against atmospheric or environmental pollution by reducing reactive oxygen species in and on the skin.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

An in vitro study was conducted to analyze the skin protecting benefits of varying concentrations of HSO and/or FSO. Particularly, the ability of HSO and/or FSO in preventing the generation of or reducing the presence of reactive oxygen species (ROS) was evaluated. Skin is often exposed to various environmental stressors, including air pollution. One of the most harmful components of air pollution is particulate matter (PM), which causes skin damage through PM-induced oxidative stress. In PM-induced oxidative stress, PM deposited in or on skin react with the skin to generate ROS in and on the skin that can lead to oxidative cell damage and cell death. Accordingly, the present in vitro study was conducted to analyze the efficacy of varying concentrations of HSO and/or FSO in reducing and/or preventing ROS in and on the skin.

To conduct the study, neonatal human epidermal keratinocytes (HEKn) were grown in standard well plates having glass bottoms coated with collagen I. The HEKn were cultured in EpiLife™ media supplemented with human keratinocyte growth supplements (HKGS), both of which are commercially available from ThermoFisher Scientific of Waltham, MA. Stock solutions of FSO, HSO, and urban dust (UD; Standard Reference Material 1649b from National Institute of Standards and Technology of Gaithersburg, MD) were prepared for the treatment of the keratinocytes. It should be appreciated that the UD was prepared by NIST from atmospheric particulate material collected in the Washington, DC area in the 70s, and is a representative of PM pollution.

The presence or amount of intracellular reactive oxygen species (ROS) was measured using fluorescence microscopy. Specifically, the keratinocytes were exposed to an oxidative stress detection reagent for about one hour in the absence (i.e., control) or presence of FSO, HSO, and/or UD. After exposure to the oxidative stress detection reagent and the FSO, HSO, and/or UD, the keratinocytes were washed twice with a wash buffer and imaged via fluorescence in the wash buffer. Live adherent cells were imaged using GFP excitation/emission filters, and the ROS levels were quantified from raw images using ImageJ software. The measured ROS levels in each of the samples are summarized in Table 1.

TABLE 1

| | | | | | Standard |
|---|---|---|---|---|---|
| | | | | ROS Levels | Error of |
| | UD | HSO | FSO | (%) Relative to | Mean |
| Sample | (μg/mL) | (%) | (%) | No Treatment | (SEM) |
|---|---|---|---|---|---|
| 1 Control | 200 | 0 | 0 | 0 | 6.35 |
| 2 | 200 | 0 | 0 | 189.54 | 4.48 |
| 3 | 200 | 1.25E−4 | 0 | −5.92 | 3.11 |
| 4 | 200 | 6.25E−5 | 0 | −0.26 | 1.17 |
| 5 | 200 | 0 | 1.25E−4 | −10.16 | 2.71 |
| 6 | 200 | 0 | 6.25E−5 | −6.9 | 1.04 |
| 7 | 200 | 1.25E−4 | 1.25E−4 | −10.39 | 1.86 |
| 8 | 200 | 1.25E−4 | 6.25E−5 | −11.82 | 1.89 |
| 9 | 200 | 6.25E−5 | 1.25E−4 | −12.25 | 1.68 |
| 10 | 200 | 6.25E−5 | 6.25E−5 | −12.85 | 1.93 |

*ROS Levels (%) Measured in Samples (1)-(10)*

As illustrated in Table 1, the combination of FSO and HSO surprisingly, unexpectedly, and significantly reduced the amount of ROS levels measured. Particularly, based on the ROS levels measured in samples (4) and (6), a decrease of about 7% was expected when the FSO and the HSO were combined in a ratio of about 1:1, as in sample (10). However, when the FSO and the HSO were combined in a ratio of about 1:1, a statistically significant decrease of about −13% (P=0.00007) was observed in sample (10).

Example 2

An in vitro study was conducted to analyze the skin protecting benefits of varying concentrations of niacinamide and/or FSO. Particularly, an in vitro study was conducted to analyze the efficacy of varying concentrations of niacinamide and/or FSO in reducing and/or preventing ROS in and on the skin.

To conduct the study, neonatal human epidermal keratinocytes (HEKn) were grown in standard well plates having glass bottoms coated with collagen I. The HEKn were cultured in EpiLife™ media supplemented with human keratinocyte growth supplements (HKGS), both of which are commercially available from ThermoFisher Scientific of Waltham, MA. Stock solutions of FSO, niacinamide, and urban dust (UD) were prepared for the treatment of the keratinocytes. It should be appreciated that the UD is representative of particulate matter (PM) pollution.

The presence or amount of intracellular reactive oxygen species (ROS) was measured using fluorescence microscopy. Specifically, the keratinocytes were exposed to an oxidative stress detection reagent for about one hour in the absence (i.e., control) or presence of FSO, niacinamide, and/or UD. After exposure to the oxidative stress detection reagent and the FSO, niacinamide, and/or UD, the keratinocytes were washed twice with a wash buffer and imaged via fluorescence in the wash buffer. Live adherent cells were imaged using GFP excitation/emission filters, and the ROS levels were quantified from raw images using ImageJ software. The measured ROS levels in each of the samples are summarized in Tables 2 and 3.

TABLE 2a

| | | ROS Levels | Standard |
|---|---|---|---|
| | | (%) Relative to | Error of Mean |
| # | Sample | No Treatment | (SEM) |
|---|---|---|---|
| 11 | Control - No Treatment; Only HEKn cells | 0 | 6.35 |

*ROS Levels (%) Measured in Samples (11) and (12)*

TABLE 2a-continued

| | | ROS Levels (%) Relative to No Treatment | Standard Error of Mean (SEM) |
|---|---|---|---|
| # | Sample | | |
| 12 | 200 µg/mL UD relative to Control | 69.77 | 5.53 |

ROS Levels (%) Measured in Samples (11) and (12)

TABLE 2b

ROS Levels (%) Measured in Samples (13)-(20)

| Sample | UD (µg/mL) | Niacinamide (%) | FSO (%) | ROS Levels (%) Relative to UD Alone | Standard Error of Mean (SEM) |
|---|---|---|---|---|---|
| 13 | 200 | 1.25E−5 | 0 | −10.79 | 2.20 |
| 14 | 200 | 6.25E−6 | 0 | −3.89 | 2.31 |
| 15 | 200 | 0 | 1.25E−4 | −9.53 | 2.17 |
| 16 | 200 | 0 | 6.25E−5 | −2.83 | 3 |
| 17 | 200 | 1.25E−5 | 1.25E−4 | −10.79 | 2.08 |
| 18 | 200 | 1.25E−5 | 6.25E−5 | −10.79 | 2.67 |
| 19 | 200 | 6.25E−6 | 1.25E−4 | −11.41 | 3.77 |
| 20 | 200 | 6.25E−6 | 6.25E−5 | −14.45 | 2.16 |

Table 2a illustrates the effects of exposing the HEKn cells to UD. As illustrated in Table 2a, exposing the HEKn cells to about 200 µg/mL of UD resulted in an increase in intracellular ROS levels of about 70% relative to HEKn cells that were not exposed to UD.

Table 2b illustrates the effects of varying concentrations of niacinamide and FSO on HEKn cells exposed to UD. As illustrated in Table 2b, when niacinamide and FSO are present in a ratio of about 1:10 a surprising, unexpected, and significant decrease in the ROS is observed. For example, based on samples (14) and (16), when combining niacinamide and FSO in a ratio of about 1:10, as in sample (20), the expected reduction in ROS was about 7%. However, a reduction of the ROS in an amount greater than about 14% was observed. As further illustrated in Table 2b, when niacinamide and FSO are present in a ratio of about 1:10, and in an amount sufficient to deliver about 1.3125E-4% or less, or about 6.875E-5% or less, to cell models, a surprising, unexpected, and significant decrease in the ROS was observed.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

We claim:

1. A personal care composition, comprising:
a carrier;
at least one plant oil comprising flaxseed oil; and
at least one vitamin B compound;
wherein the flaxseed oil and the at least one vitamin B compound are each present in an effective amount to reduce reactive oxygen species in skin;
wherein a total weight of the at least one vitamin B compound and the flaxseed oil is less than or equal to about 6.875E-5 weight %, based on a total weight of the personal care composition; and
wherein the at least one vitamin B compound and the flaxseed oil are present in a weight ratio of about 1:10.

2. The personal care composition of claim 1, wherein the at least one vitamin B compound comprises one or more of a vitamin B1 compound, a vitamin B2 compound, a vitamin B3 compound, a vitamin B5 compound, a vitamin B6 compound, or combinations thereof.

3. The personal care composition of claim 2, wherein the at least one vitamin B compound comprises the vitamin B3 compound.

4. The personal care composition of claim 3, wherein the at least one vitamin B compound consists of the vitamin B3 compound.

5. The personal care composition of claim 3, wherein the vitamin B3 compound comprises niacinamide.

6. The personal care composition of claim 1, wherein the at least one plant oil further comprises one or more of palm kernel oil, coconut oil, avocado oil, canola oil, corn oil, cottonseed oil, olive oil, palm oil, high-oleic sunflower oil, mid-oleic sunflower oil, sunflower oil, palm stearin oil, palm kernel olein oil, safflower oil, babassu oil, sweet almond oil, castor oil, canola oil, soybean oil, olive oil, acai oil, andiroba oil, apricot kernel oil, argan oil, passion fruit oil, marula oil, mango oil, shea oil, macadamia nut oil, brazil nut oil, borage oil, copaiba oil, grape seed oil, buriti oil, sesame oil, blueberry oil, cranberry oil, blackberry oil, plum oil, raspberry oil, camelina oil, camellia oil, walnut oil, wheat germ oil, calendula oil, cherry kernel oil, cucumber seed oil, papaya oil, aloe vera oil, hemp oil, hemp seed oil, or combinations thereof.

7. The personal care composition of claim 1, wherein the at least one plant oil comprises a natural oil.

8. The personal care composition of claim 1, wherein the carrier is a solid carrier.

9. The personal care composition of claim 1, wherein the carrier is a liquid carrier.

10. A method for treating or reducing reactive oxygen species in or on skin, the method comprising contacting the skin with the personal care composition of claim 1.

11. The personal care composition of claim 1 for use in treating or reducing reactive oxygen species in or on skin.

* * * * *